United States Patent [19]

Chen

[11] Patent Number: 4,728,321

[45] Date of Patent: Mar. 1, 1988

[54] SYRINGE CAP WITH ADHESIVE HOLDING PLUG

[75] Inventor: Chang-Cheng Chen, Pingtung Hsien, Taiwan

[73] Assignee: Ming-Chiu Wu, Taiwan

[21] Appl. No.: 39,067

[22] Filed: Apr. 16, 1987

[51] Int. Cl.[4] .............................................. A61M 5/00
[52] U.S. Cl. ................................................... 604/110
[58] Field of Search ............... 604/110, 187, 192, 197, 604/198, 263

[56] References Cited

U.S. PATENT DOCUMENTS 4,121,588 10/1978 Geiger .................................. 604/110
4,392,859 7/1983 Dent ..................................... 604/198
4,482,348 11/1984 Dent ..................................... 604/198

Primary Examiner—John D. Yasko
Attorney, Agent, or Firm—Lowe, Price, LeBlanc, Becker & Shur

[57] ABSTRACT

A syringe cap for a used syringe comprises a hollow cap body to be mounted on a syringe for encasing a syringe needle and an adhesive holding plug means mounted slideably on the cap body for moving between an extended position and a closed position. The plug means is cemented permanently to the used needle by means of an adhesive held in the plug when the needle pierces a closed end of the plug.

1 Claim, 3 Drawing Figures

SYRINGE CAP WITH ADHESIVE HOLDING PLUG

BACKGROUND OF THE INVENTION

The present invention relates to a syringe cap for capping a used syringe and, more particularly, to a syringe cap with an adhesive holding plug means to be cemented permanently to a used syringe needle.

Syringes of varying materials are well-known in the art of medical treatment, such as, those made of glass or plastic. Plastic syringes are convenient to use since they are cheap and can be discarded after use. However, proper disposal of used syringes remains to be a problem because the needles of the used syringes may injure an individual. U.S. Pat. No. 4,634,428 to Cwo-Liang Cuu discloses a cover for a used syringe which includes a hollow cover body to be mounted on and encase the needle of the syringe and a telescopic needle destroying cap mounted slideably to one end of the cover body. When an impact force is applied to the cap, the cap destroys or bends the needle and then retain the bend needle in a bulbous lip at the interior suface of the cap. Although, the cap can enclose the bend needle permanently, it can not be manufactured easily.

SUMMARY OF THE INVENTION

It is therefore a main object of the present invention to provide a syringe cap of simple construction which can be manufactured more easily than the above described prior syringe cap.

According to the present invention, a syringe cap comprises a hollow cap body having a surrounding wall for encasing a needle of a syringe, a first open end to be mounted on the syringe and a second open end to extend beyond the needle, and an adhesive holding plug means mounted slideably on the second open end for moving between an extended position and a retracted position, the means having an outer closed end, an opposite inner closed end that can pierced by the needle, and a cavity closed by said first and second closed ends and containing an adhesive. The inner closed end of the adhesive holding plug is pierced by the needle when a force is applied on the plug means, and the adhesive cements the needle to the plug means permanently.

The exemplary preferred embodiment will be described in detail with reference to the following drawings, in which:

DETAILED DESCRIPTION OF THE PREFERRED EMBODIMENT

Figure 1:
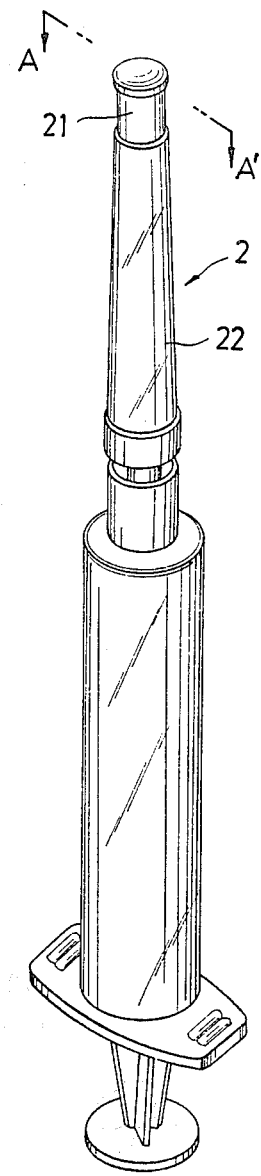
FIG. 1 is a perspective view of a syringe incorporating a syringe cap of the invention.
Figure 2:
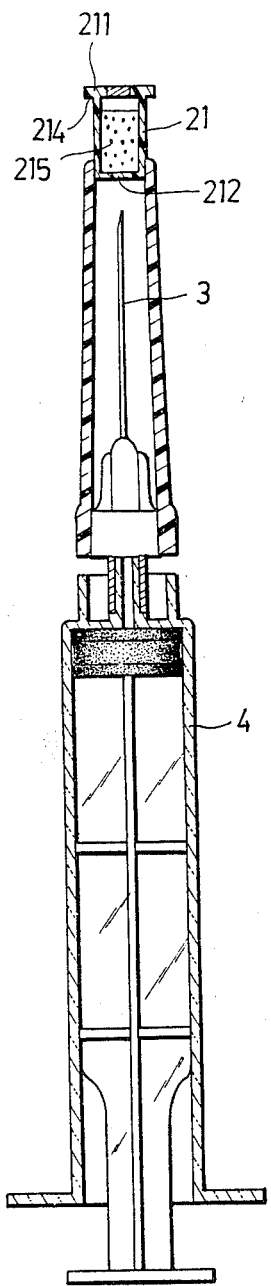
FIG. 2 is a sectional view taken along line A—A' of FIG. 1.

Referring to the drawings, a syringe cap 2 of a preferred embodiment is shown, having a substantially cylindrical hollow cap body 22 for encasing a needle 3 of a syringe 4. The cap body 22 has one open end thereof mounted on the syringe 4. Another open end of the syringe 4 extends beyond the end of the needle 3.

An adhesive holding plug means 21 of substantially cylindrical hollow body is mounted slideably on the top open end 221 of the cap body 2. The plug means 21 has an outer closed end 211, an inner closed end 212 and a closed cavity 213 containing an adhesive 215. The outer closed end 211 is provided with an access opening receiving a cover member 216 through which the adhesive can be put into the cavity 213, and a flange 214 to abut with the top end of the cap body when the plug means 21 retracts in the cap body 22 upon impact.

When an impact force is applied on the plug means 21 to retract the plug means 21 in the cap body 22, the needle pierces the inner closed end 212 of the plug means 21 and extends into the adhesive 215, thereby cementing permanently the plug means 21 to the syringe needle.

Figure 3:
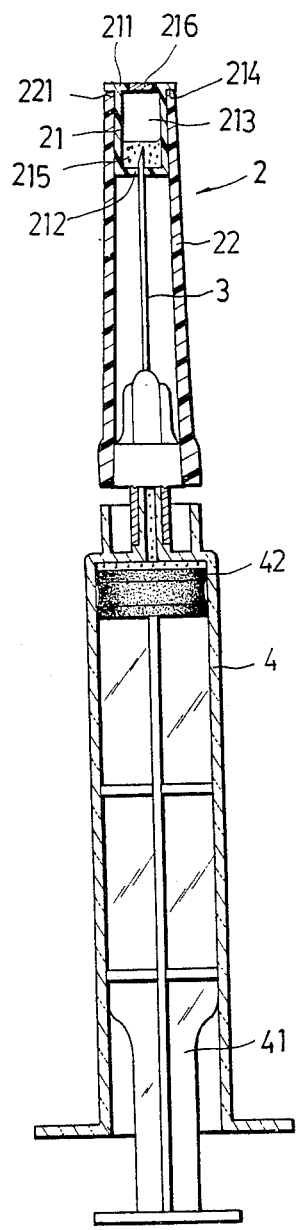
FIG. 3 is a sectional view showing that the syringe needle is cemented to the plug means of the syringe cap.

When a piston 42 of the syringe 4 is moved to a suctioning position by pulling a handle 41 as shown in FIG. 3, some adhesive 215 will be drawn into the body of the syringe 4. As such, the interior of the needle will be blocked up by the adhesive and the piston 42 may become immovable or inoperative as it is adhesively bonded to the inner side of the wall of the syringe 4. Accordingly, the syringe needle capped thereby can never be reused.

The adhesive 215 may be an adhesive which has a high strength bonding ability to a metal, for example, an epoxy resin based adhesive. The adhesive 215 will give a permanent cementing effect for the plug means and the used needle after the adhesive is cured.

With the invention thus explained, it is apparent that various modifications and variations can be made without departing from the scope of the invention. It is therefore intended that the invention be limited as indicated in the appended claims.

What I claim is:

1. A syringe cap comprising:
   a hollow cap body having a surrounding wall for encasing a needle of a syringe, a first open end to be mounted on the syringe and a second open end to extend beyond the needle;
   an adhesive holding plug means mounted slideably on said second open end for moving between an extended position and a retracted position, said means having an outer closed end, an opposite inner closed end that can be pierced by the needle, and a cavity closed by said inner and outer closed ends; and
   an adhesive contained in said cavity,
   said inner closed end being pierced by the needle when a pressure is applied on said plug means, and said adhesive means bonding said needle to said plug means.

* * * * *